United States Patent [19]

Tang et al.

[11] 4,229,378
[45] Oct. 21, 1980

[54] PROCESS FOR THE PRODUCTION OF 1-PHENYL-3-(3-TRIFLUOROMETHYL-PHENYL)-2-PROPANONE

[75] Inventors: David Y. Tang, Eggertsville; Arthur M. Foster, Snyder, both of N.Y.

[73] Assignee: Hooker Chemicals & Plastics Corp., Niagara Falls, N.Y.

[21] Appl. No.: 38,766

[22] Filed: May 14, 1979

[51] Int. Cl.$^3$ ............................................. C07C 45/16
[52] U.S. Cl. ............................... 568/313; 260/348.31; 568/841; 568/867
[58] Field of Search ...................... 260/590 D, 348.31; 568/841, 867

[56] References Cited

U.S. PATENT DOCUMENTS

| | | | |
|---|---|---|---|
| 2,326,068 | 8/1943 | Rohrmann | 260/590 D |
| 3,641,058 | 2/1972 | Corrigan et al. | 260/591 |
| 3,928,421 | 12/1975 | Kyogoku et al. | 260/590 D |

Primary Examiner—Joseph E. Evans
Assistant Examiner—James H. Reamer
Attorney, Agent, or Firm—Peter F. Casella; William J. Crossetta, Jr.; Arthur S. Cookfair

[57] ABSTRACT

The present invention provides a novel process for the production of 1-phenyl-3-(3-trifluoromethylphenyl)-2-propanone. The process comprises the steps of:
(a) condensing 3-trifluoromethylbenzaldehyde with acetophenone under basic conditions to form a substituted chalcone,
(b) epoxidation of the substituted chalcone to produce the corresponding epoxide,
(c) converting the epoxide to a chlorohydrin,
(d) catalytic hydrogenolysis of the chlorohydrin to produce a diol and subsequently converting the diol into the corresponding alcohol, and
(e) oxidizing the alcohol to produce 1-phenyl-3-(3-trifluoromethylphenyl)-2-propanone.

8 Claims, No Drawings

PROCESS FOR THE PRODUCTION OF 1-PHENYL-3-(3-TRIFLUOROMETHYLPHENYL)-2-PROPANONE

The present invention relates to the preparation of 1-phenyl-3-(3-trifluoromethylphenyl)-2-propanone.

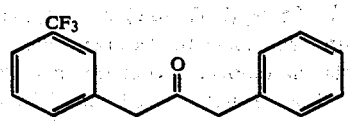

1-phenyl-3-(3-trifluoromethylphenyl)-2-propanone is an intermediate useful in the production of 3-phenyl-4-piperidinones, such as 1-methyl-3-phenyl-5-[3-trifluoromethyl phenyl]-4(1H)-pyridinone

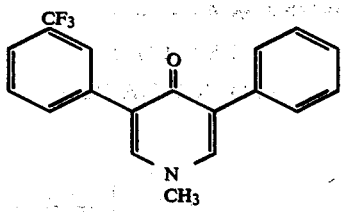

3-phenyl-4-piperidinones are useful herbicides, especially for the preemergent control of foxtail and bindweed. Examples of such piperidinones and their herbicidal properties are described in detail in German Offenlegungsschrift No. 2,537,753 (Mar. 11, 1978) and in German Offenlegungsschrift No. 2,628,992 (Jan. 20, 1977).

1-phenyl-3-(3-trifluromethylphenyl)-2-propanone may be reacted with ethyl formate and methylamine in the presence of hydrochloric acid to produce useful pyridinones, for example:

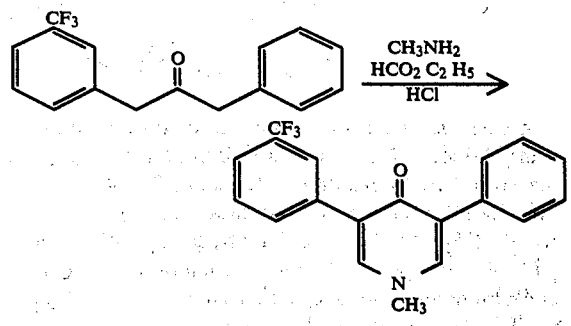

BRIEF DESCRIPTION OF THE INVENTION

The present invention provides a novel process for the production of 1-phenyl-3-(3-trifluoromethylphenyl)-2-propanone. The process comprises the steps of:

(a) condensing 3-trifluoromethylbenzaldehyde with acetophenone under basic conditions to form a substituted chalcone,
(b) epoxidation of the substituted chalcone to produce the corresponding epoxide,
(c) converting the epoxide to a chlorohydrin,
(d) catalytic hydrogenolysis of the chlorohydrin to produce a diol and subsequently converting the diol into the corresponding alcohol, and
(e) oxidizing the alcohol to produce 1-phenyl-3-(3-trifluoromethylphenyl)-2-propanone.

With reference to step (a), the reaction is preferably carried out utilizing stoichiometric amounts of 3-trifluoromethylbenzaldehyde and acetophenone at reaction temperatures between about 15° and about 30° C. The substituted chalcone product of step (a) is phenyl (3-trifluoromethylphenyl)styryl ketone and preferably is produced at a yield of 90% or more of theoretical.

With reference to step (b), the reaction is preferably carried out under basic conditions at reaction temperatures of ambient or below. The corresponding epoxide produced is phenyl alpha, beta-epoxy-beta-(3-trifluoromethylphenyl)ethyl ketone and preferably is produced at a yield in the range of 90% of theoretical.

With reference to step (c), the conversion is preferably carried out in the presence of a chloride such as stannic chloride or hydrogen chloride. The chlorohydrin product is phenyl beta-chloro-alpha-hydroxy-beta-(3-trifluoromethylphenyl)ethyl ketone and is preferably produced in yields in the range of 70% or more of theoretical.

With reference to step (d), preferably an initial hydrogenolysis is carried out at room temperature under a pressure of about 45 psig of hydrogen to produce 1-phenyl-3-(3-trifluoromethylphenyl)-1,2-propane diol and subsequently a second hydrogenolysis is carried out at a temperature of about 60° C. under a pressure of about 60 psig to produce 1-phenyl-3-(3-trifluoromethylphenyl)-2-propanol. It will be understood that the initial and subsequent hydrogenolysis stages if desired may be conducted as a single step without interruption or separation to produce 1-phenyl-3-(3-trifluoromethylphenyl)-2-propanol. Suitable catalysts are those known in the art, for example, platinum or palladium on supports, such as carbon. The hydrogenolysis product may include 1-phenyl-3-(3-trifluoromethylphenyl)-propane in amounts of up to about 20% by weight, with yields of about 80% of the desired alcohol.

With reference to step (e), the alcohol product of step (d) may be oxidized by known techniques to produce the desired 1-phenyl-3-(3-trifluoromethylphenyl)-2-propanone product.

DETAILED DESCRIPTION OF THE INVENTION

The following examples are illustrative of the sequential steps of the present process:

EXAMPLE 1

CONDENSATION

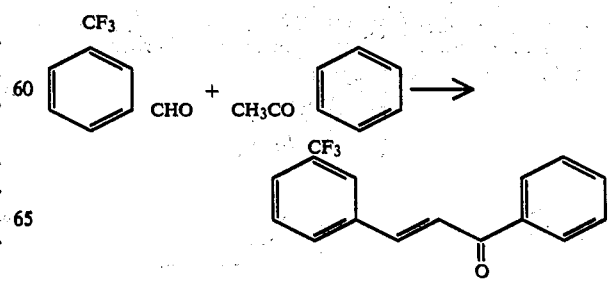

A solution of 13 gm (0.33 mole) of sodium hydroxide, 100 ml of water and 60 ml of 95% ethyl alcohol was placed in a 500 ml 3-necked flask cooled in an ice bath. The flask was equipped with a thermometer, a condenser and a mechanical stirrer. Into the alkaline solution 30 g (0.25 mole) of acetophenone was quickly added with stirring. Subsequently, 43.5 g (0.25 mole) of 3-trifluoromethylbenzaldehyde was similarly added. The temperature was maintained between about 15° and about 30° C. After 2.5 hours, the stirrer was removed and the mixture left in a refrigerator overnight. A solid paste product was removed by filtration using a Buchner funnel and washed with water until the washings were neutral to litmus. After thorough drying in a vacuum desicator, the crude substituted chalcone product was found to weigh 65 g (94% of theoretical yield). The product was identified by NMR and IR spectrographic analyses to be (3-trifluoromethylphenyl)benzalacetophenone, or in alternate nomenclature, phenyl (3-trifluoromethylphenyl)styryl ketone. The recovered product was found to be sufficiently pure and eminently satisfactory for use in the subsequent process steps.

EXAMPLE 2
EPOXIDATION

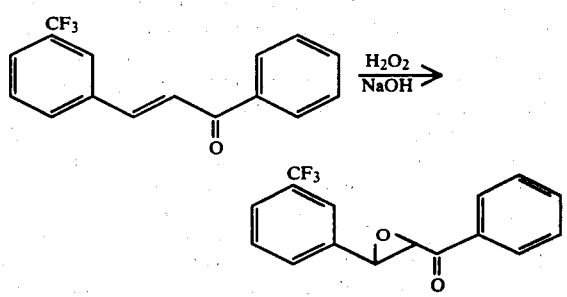

27.6 g (0.1 mole) of the product of Example 1 was placed into solution with 300 ml of methyl alcohol. 25 ml 2N sodium hydroxide were added with stirring and cooling. Subsequently, 34 ml of 15% hydrogen peroxide were added drop-wise. After completion of the peroxide addition, the mixture was stirred for 2 hours at ambient temperature. A white suspension formed. The suspension was poured into 1 liter of water and subsequently separated by filtration using a Buchner funnel. The white solid product was washed with water until the washings were neutral to litmus and subsequently dried in a vacuum desicator. The crude epoxide product was found to weigh 26.1 g (90% of the theoretical yield) and had a melting point between about 76.5° and about 78.5° C. The structure of the epoxide was confirmed by NMR and IR spectral analyses to be phenyl alpha,beta-epoxybeta-(3-trifluoromethylphenyl)ethyl ketone, or in alternative nomenclature, 2-benzoyl-3-(3-trifluoromethylphenyl)oxacyclopropane.

EXAMPLE 3
CONVERSION

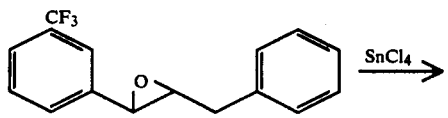

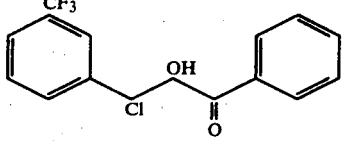

A solution of 5.9 g (0.02 mole) of the epoxide product from Example 2 and 250 ml of toluene was treated with 6.5 ml of stannic chloride. After the mixture had been stirred for 1 hour, it was poured into 300 g of ice. The organic layer was then separated, washed with water, dried over MgSO₄ and concentrated using a rotary evaporator. 4.8 g (73% of theoretical) of the chlorohydrin product was recovered. The structure of this product was confirmed by NMR and IR spectral analyses to be phenyl beta-chloro-alpha-hydroxy-beta-(3-trifluoromethylphenyl)ethyl ketone.

EXAMPLE 4
HYDROGENATION

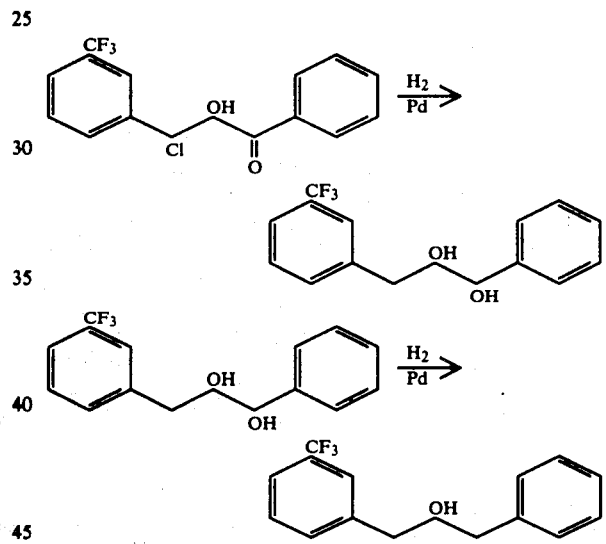

A solution of 1.12 g (3.4 mm mole) of the chlorohydrin product of Example 3 and 30 ml of methanol were placed in a hydrogenation bottle and 0.2 g of 5% palladium catalyst on a carbon base was added. The mixture was hydrogenated using a Parr hydrogenator under 45 psig of hydrogen at ambient temperature. After the consumption of hydrogen slowed, the white solid product was separated and by ¹H NMR and IR spectrographic techniques was found to be 1-phenyl-3-(3-trifluoromethylphenyl)-1,2-propan-diol. This product was subsequently returned to the hydrogenator and hydrogenolysis tinued as the pressure was raised to 60 psig and the temperature raised to 60° C. for a period of 2 hours. The catalyst was removed by filtration and the solvent evaporated. 0.8 g of a crude colorless oil was recovered. Analyses by NMR and GPC showed the product to contain about 80% by weight of 1-phenyl-3-(3-trifluoromethylphenyl)-2-propanol and about 20% by weight of 1-phenyl-3-(3-trifluoromethylphenyl)-propane.

EXAMPLE 5
OXIDATION

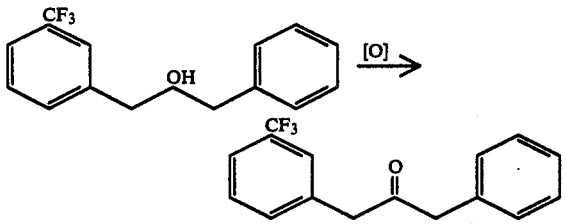

1.2 g (4.3 mm mole) of the alcohol product of Example 4 was added rapidly to a stirred solution of 1.7 g (7.9 mm mole) of pyridinum chlorochromate in 27 ml of dichloromethane. After 1.5 hours, a black mixture was obtained and was diluted with 5 volumes of diethyl ether and the organic layer separated. The solvent was evaporated using a rotary evaporator to yield 0.98 (80% of theoretical) of the desired propanone, 1-phenyl-3-(3-trifluoromethylphenyl)-2-propanone. The structure of 1-phenyl-3-(3-trifluoromethylphenyl)-2-propanone was confirmed by NMR, IR and GPC analyses.

The foregoing description and embodiments are intended to illustrate the invention without limiting it thereby. It will be understood that various modifications can be made in the invention without departing from the spirit or scope thereof.

What is claimed is:

1. A method of making 1-phenyl-3-(3-trifluoromethylphenyl)-2-propanone comprising the steps of:
   (a) condensing 3-trifluoromethylbenzaldehyde with acetophenone under basic conditions to produce a substituted chalcone,
   (b) epoxidizing said substituted chalcone to produce the corresponding epoxide,
   (c) converting the epoxide to a chlorohydrin,
   (d) hydrogenating said chlorohydrin to produce a diol and subsequently converting said diol into the corresponding alcohol, and
   (e) oxidizing said alcohol to produce 1-phenyl-3-(3-trifluoromethylphenyl)-2-propanone.

2. The process of claim 1 wherein the product of step (a) is phenyl (3-trifluoromethylphenyl)styryl ketone.

3. The process of claim 1 wherein step (a) is carried out at temperatures between about 15° and about 30° C.

4. The process of claim 1 wherein the product of step (b) is phenyl alpha,beta-epoxy-beta-(3-trifluoromethylphenyl)ethyl ketone.

5. The process of claim 1 wherein the product of step (c) is phenyl beta-chloro-alpha-hydroxy-beta-(3-trifluoromethylphenyl)ethyl ketone.

6. The process of claim 1 wherein step (d) is carried out in the presence of a catalyst.

7. The process of claim 1 wherein the diol of step (d) is 1-phenyl-3-(3-trifluoromethylphenyl)-1,2-propandiol.

8. The process of claim 1 wherein the alcohol of step (d) is 1-phenyl-3-(3-trifluoromethylphenyl)-2-propanol.